(12) United States Patent
Kanitz et al.

(10) Patent No.: US 8,309,284 B2
(45) Date of Patent: Nov. 13, 2012

(54) HIGHLY CONDUCTIVE ORGANIC CHARGE CARRIER TRANSPORT MATERIAL

(75) Inventors: Andreas Kanitz, Höchstadt (DE); Jürgen Adler, Röttenbach (DE); Ralf Krause, Dresden (DE); Günter Schmid, Hemhofen (DE)

(73) Assignee: Osram Opto Semiconductors GmbH, Regensburg (DE)

( * ) Notice: Subject to any disclaimer, the term of this patent is extended or adjusted under 35 U.S.C. 154(b) by 630 days.

(21) Appl. No.: 12/514,986

(22) PCT Filed: Nov. 12, 2007

(86) PCT No.: PCT/EP2007/062210
§ 371 (c)(1),
(2), (4) Date: Dec. 22, 2009

(87) PCT Pub. No.: WO2008/058929
PCT Pub. Date: May 22, 2008

(65) Prior Publication Data
US 2010/0112471 A1     May 6, 2010

(30) Foreign Application Priority Data
Nov. 14, 2006   (DE) .......... 10 2006 053 644

(51) Int. Cl.
*G03G 15/02* (2006.01)
*H01L 21/00* (2006.01)
(52) U.S. Cl. .......... 430/58.5; 257/40; 257/E51.018; 257/E51.024; 430/58.05; 438/46

(58) Field of Classification Search ............ 257/40, 257/E51.018, E51.024; 430/58.05, 58.5; 438/46
See application file for complete search history.

(56) References Cited

U.S. PATENT DOCUMENTS
5,948,551 A * 9/1999 Gompper et al. .......... 428/690

FOREIGN PATENT DOCUMENTS
EP    0 690 052    1/1996

OTHER PUBLICATIONS

R. Gompper et al., "Synthesis of Oligo (diazaphenyls), Tailor-Made Fluorescent Heteroaromatics and Pathways to Nanostructures", Synthesis, vol. 6, pp. 696-708, 1997.

\* cited by examiner

*Primary Examiner* — Bijan Ahvazi
(74) *Attorney, Agent, or Firm* — Cozen O'Connor

(57) ABSTRACT

An organic, semiconducting material, in particular, a material which can be used as a semiconductor material in organic electronics. A component of the material thereby comprises the oligophenylene from heterocyclic parent compounds with the following structure:

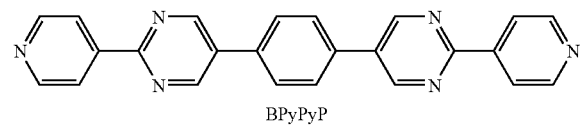

BPyPyP

5 Claims, 2 Drawing Sheets

Current-voltage characteristic curve

UV/VIS spectrum in THF  $\lambda_{max} = 317$ nm

Key:  1  Absorbance

PL spectrum in THF  $\lambda_E = 389nm$

Key: 2    Intensity

HIGHLY CONDUCTIVE ORGANIC CHARGE CARRIER TRANSPORT MATERIAL

RELATED APPLICATIONS

This is a U.S. national stage under 35 USC §371 of application No. PCT/EP2007/062210, filed on Nov. 12, 2007.

This application claims the priority of German Patent Application No. 10 2006 053 644.4 filed Nov. 14, 2006 the entire content of which is hereby incorporated by reference.

FIELD OF THE INVENTION

The invention concerns an organic material, in particular, a material which can be used as a semiconductor material or conductive material in organic electronics.

BACKGROUND OF THE INVENTION

Organic semiconductor materials are subdivided into hole and electron transport materials. They are needed for the manufacturing of organic electronic components, such as organic light-emitting diodes (OLEDs), organic field effect transistors (OFETs), and/or organic solar cells.

On the side of hole transport materials, very efficient and stable structures have been developed in the last 15 years which, depending on the application with the most varied hole injection characteristics, are available and, in the hole-transporting, oxidized state, form stable radical cations.

On the side of electron transport materials, there have been up to now only very few representatives which meet the high requirements for electron transport materials for organic electronics. At present, the derivatives of phenanthrolin (BCP and BPhen) and derivatives of oxadiazole are considered good electron conductors. Radical-anionic species, which are formed during the operation of these components, bring about a configuration change in the heterocyclic structures, so that the electron transport characteristic declines as a consequence of the formation of conjugation interruptions.

The known materials exhibit deficits both in the bandwidth of the electron injection and also in their stability in the electron-transporting, reduced state, so that, in particular, the radical anions cannot be formed reversibly over a longer time period.

As a rule, the semiconducting characteristics of the materials are attained by doping, because the base materials alone are never conductive enough.

SUMMARY OF THE INVENTION

One object of the invention is to create an organic electron transport material, in which the bandwidth of the electron injection and also the stability in the electron-transporting, reduced state is improved, in comparison to known materials. Another aspect of the invention is to create a material which can form radical anions reversibly over a longer time period.

To attain these objects, an efficient electron conductor was developed which is characterized by a larger injection bandwidth and above all, by the capability of forming reversible radical anions of a high stability.

One aspect of the invention is directed to an organic charge transport material, with which electrons and holes can be transported equally well, wherein in a layer of the undoped material, with a thickness of 150 nm, a measurable current density of greater than/equal to 0.5 A/cm² is already obtained at 0.25 V.

The invention can be applied to an organic semiconducting material, which comprises oligophenylenes from heterocyclic parent compounds of the following structure:

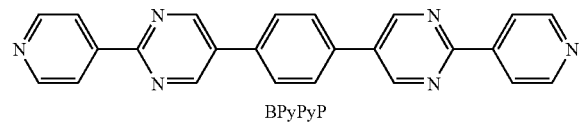

BPyPyP

A BPyPyP material with the structure of an oligophenylene, shown above, which is organic in the original sense—that is, contains only carbon, nitrogen, and hydrogen—exhibits a characteristic which is unusual for purely organic materials (that is, only C, H, and N-containing structures), with a conductivity which up to now has been unattained by several orders of magnitude, in which electrons and holes are equally transported.

In particular, with a layer with a thickness of 150 nm, current densities of 0.6 A/cm² are attained at 0.25 V in the positive and negative directions.

According to a particularly advantageous embodiment, the layer is thereby transparent, with particular preference transparent in the entire visible spectral range.

The current density attained here in the undoped material corresponds to a current density which has been attained up to now only by so-called doped systems.

In addition to the complicated process steps for the doping, what is also disadvantageous in the doped materials is that they usually form, with the doping, a charge transfer complex and absorb in the long-wave range of the visible spectrum—that is, are not transparent. Both disadvantages are overcome, in accordance with an embodiment of the invention, by using this single component, the BPyPyP, in the material.

Therefore, this BPyPyP material can be used directly, instead of an n-doped electron transport matrix, to improve the injection of electrons from the cathode in an organic electronic component.

According to an advantageous embodiment of the invention, the BPyPyP material is deposited by co-evaporation with n-doping materials or N-doping agents as an even more highly conductive layer.

Since the BPyPyP material is an excellent electron transporter, it is possible to use it in this function in all organic electronic components and arrangements.

Moreover, the material can be used both in OLED arrangements and an ambipolar matrix alone and in any mixtures (blends) for any emitter materials.

On the other hand, transparent electrodes can also be produced on any substrates which have the anodic and/or cathodic function, from the material and from mixtures with this material.

The excellent current transport appears to come about by a self-organizing, orderly deposition of the molecules by the evaporation process.

DETAILED DESCRIPTION OF THE DRAWINGS

Figure 1:
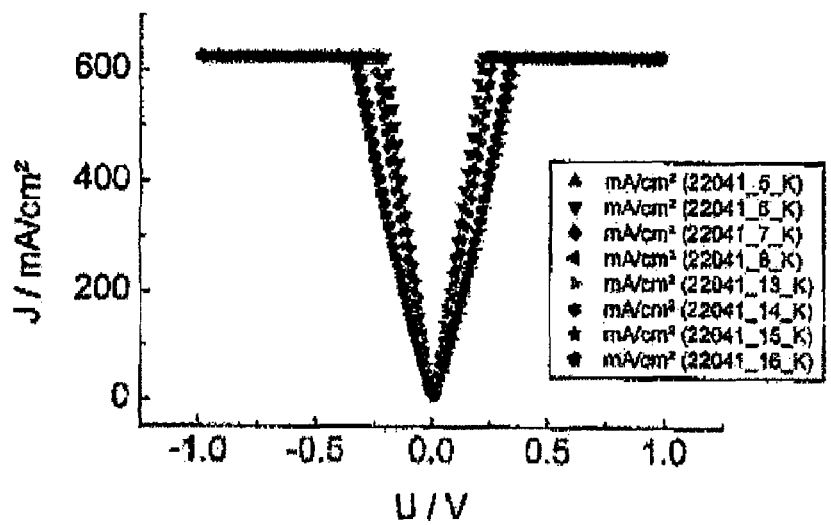
FIG. 1 shows the current-voltage characteristic curve, from which one can see how the conductivity of the material is manifested in the positive and negative voltage field.
Figure 2:
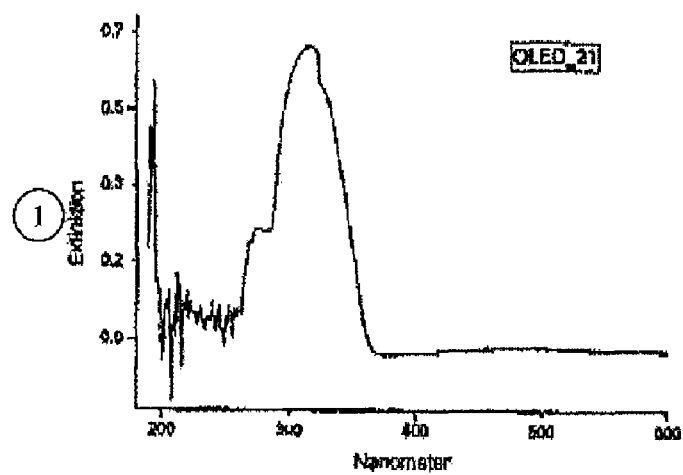
FIG. 2 shows the transparency of the material in the UV/VIS spectrum.
Figure 3:
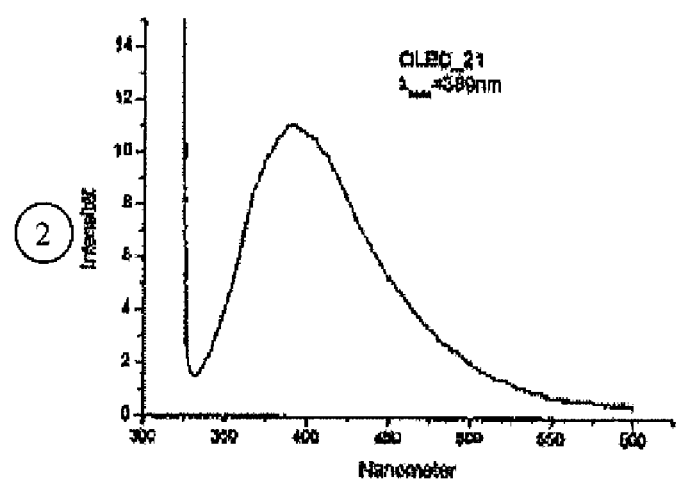
FIG. 3 shows a photoluminescence spectrum of the compound.

A typical structure of an organic electronic component comprises a substrate, a lower electrode, the semiconducting organic layer, and an upper anode. With an analogous structure, the measurement data contained in the figures were obtained. In the example shown, the substrate was made of glass; the lower electrode, of indium-tin oxide (ITO); the semiconducting organic layer was a layer of BPyPyP, with a thickness of 150 nm, with a second electrode, above, consisting of an aluminum layer, with a thickness of 100 nm.

EMBODIMENTS

Preparation of bis-2-(4-pyridyl)pyrimid-5-yl-1,4-phenylene-1) 4-pyridine carboxamidine hydrochloride 1

4-Cyanopyridine (50.0 g, 470 mmol, 1 equivalent), together with sodium methanolate (3.0 g, 53 mmol, 0.11 equivalent), is stirred in ca. 230 mL dry methanol, for 1.5 h, at RT, in a 500-mL flask. Ammonium chloride (27.7 g, 52 mmol, 1.1 equivalent) is added to the whitish suspension and stirring is carried out for at least another 24 h. The nice, finely distributed, white precipitate is suctioned off, and the mother liquor is concentrated to dryness on the rotary evaporator. The filter cake is combined with the residue from the mother liquor and dissolved and recrystallized. After the suctioning and washing with ether, the product is dried in a vacuum at RT.

Yield: 70.5 g (95% of the theoretical), white crystals, M=157.6 g·mol$^{-1}$; melting point: 250° C.

2) Bis(1,4-phenylene)-2-(3-dimethylamino-2-propene dimethyliminium)diperchlorate 2

DMF (200 mL, 2.5 mol, 30 equivalents) is present in a 1000-mL three-neck flask, with a thermometer, dropping funnel, and reflux condenser with a mounted drying tube, and is cooled to ca. 0° C. by means of an ice/salt cooling mixture. While stirring, phosphoroxychloride (46 mL, 0.5 mol, 6 equivalents) is slowly dripped in, wherein the temperature may not rise above 0° C. Stirring is subsequently carried out for 10 min and 1,4-phenylenediacetic acid (16.3 g, 0.08 mol, 1 equivalent) are added to the reactive mixture. Then, the solution is heated to 90° C. for 6 h, cooled, and poured onto 1 kg ice. For the precipitation of the product, sodium perchlorate (30.8 g, 0.25 mol, 3 equivalents), dissolved in a quantity of water, is added to the aqueous solution, while stirring. The precipitate is suctioned off, mixed with methanol/ether and washed with pure ether, and subsequently dried in a vacuum.

Yield: 31.5 g (71% of the theoretical), white crystals M=527.4 g·mol$^{-1}$; melting point: 292-296° C.

3) Bis-2-(4-pyridyl)pyrimid-5-yl-1,4-phenylene

4-Pyridine carboxamidine hydrochloride 1 (5.5 g, 35 mmol, 2.2 equivalents), together with the phenylene bisvinamidinium salt 2 (8.3 g, 18 mmol, 1 equivalent) are heated in pyridine, for 8 h, at relative humidity, in a 250-mL flask. The brown-yellow precipitate formed is suctioned off; washed with methanol, methanol/ether, and pure ether; and dried in a vacuum at RT. A dissolving and recrystallization can be carried out from DMSO. Subsequently, the product is sublimated at 320° C.

Yield: 4.5 g (74% of the theoretical), pale-yellow, needle-shaped crystals M=388.4 g·mol$^{-1}$; melting point: >310° C.; DC: silica gel/THF, $R_F$=0.81

Analysis: $^1_H$-NMR

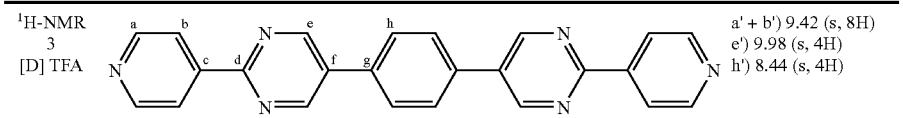

$^1$H-NMR
3
[D] TFA a' + b') 9.42 (s, 8H)
e') 9.98 (s, 4H)
h') 8.44 (s, 4H)

The invention concerns an organic, semiconducting material, in particular, a material which can be used as a semiconductor material or a conducting material in organic electronics. A component of the material thereby comprises the oligophenylene from heterocyclic parent compounds with the following structure:

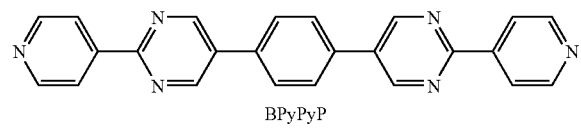

BPyPyP

The scope of protection of the invention is not limited to the examples given hereinabove. The invention is embodied in each novel characteristic and each combination of characteristics, which includes every combination of any features which are stated in the claims, even if this feature or combination of features is not explicitly stated in the examples.

The invention claimed is:

1. An organic charge transport material, with which electrons and holes can be transported equally well, wherein in a layer of undoped material, with a thickness of 150 nm, a measurable current density of larger than/equal to 0.5 A/cm$^2$ is exhibited at 0.25 V,
    wherein the charge transport material comprises an oligophenylenes compound from heterocyclic parent compounds with the following structure

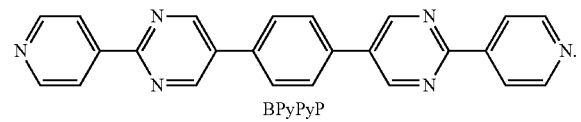

BPyPyP

2. The charge transport material according to claim 1, wherein the material is transparent in thin films.

3. The charge transport material according to claim 1, which is present as a mixture.

4. The charge transport material according to claim 1, which is present n- or p-doped.

5. An organic electronic component with a semiconducting layer and/or a conductive layer comprising the charge transport material according to claim 1.

* * * * *